United States Patent [19]

Kosak

[11] Patent Number: 4,645,498
[45] Date of Patent: Feb. 24, 1987

[54] HOT OR COLD COMPRESS WITH BLADDER ENCLOSURE

[76] Inventor: Imogene Kosak, 1042 Shunpike Rd., Cape May, N.J. 08204

[21] Appl. No.: 702,974

[22] Filed: Feb. 19, 1985

[51] Int. Cl.⁴ ............................................. A61M 35/00
[52] U.S. Cl. .................................. 604/289; 128/403; 128/DIG. 15
[58] Field of Search ....................... 604/290, 291, 289; 128/DIG. 15, 399–403, 157, 165, 327

[56] References Cited

U.S. PATENT DOCUMENTS

| | | | |
|---|---|---|---|
| 3,628,537 | 12/1971 | Berndt et al. | 128/403 |
| 3,834,396 | 9/1974 | Foster | 128/403 |
| 4,055,188 | 10/1977 | Pelton | 128/403 |
| 4,527,566 | 7/1985 | Abare | 128/403 |

OTHER PUBLICATIONS

Catalog Cut, "Healthcore", OmniPak, Baka Manufacturing Co., Plainville, Mass., 6/1982, avail.

*Primary Examiner*—C. Fred Rosenbaum
*Assistant Examiner*—J. L. Kruter
*Attorney, Agent, or Firm*—Norman E. Lehrer

[57] ABSTRACT

A compress capable of delivering hot or cold, wet or dry temperature treatment to a person's body. The compress is formed from a pair of rectangularly shaped waterproof panels which are joined together around their peripheries to form a hollow space therebetween. One of said panels has an elongated opening to allow for the introduction of ice, hot water, a wet towel or the like and also carries a closure flap for closing the opening. The other panel has a portion thereof formed of a porous fabric material so that liquid from within the hollow space can seep therethrough. Located within the hollow space is a flexible waterproof bladder which also has an opening adjacent the opening in the panel. If a dry compress is desired, the bladder is expanded to fill the space between the panels and is filled with ice or hot water. If a wet compress is desired, the bladder is rolled or folded out of the way and ice or a hot wet towel is placed directly into the space between the panels. The compress can be wrapped around a person's leg or arm and held in place with Velcro fasteners carried by the panels.

1 Claim, 6 Drawing Figures

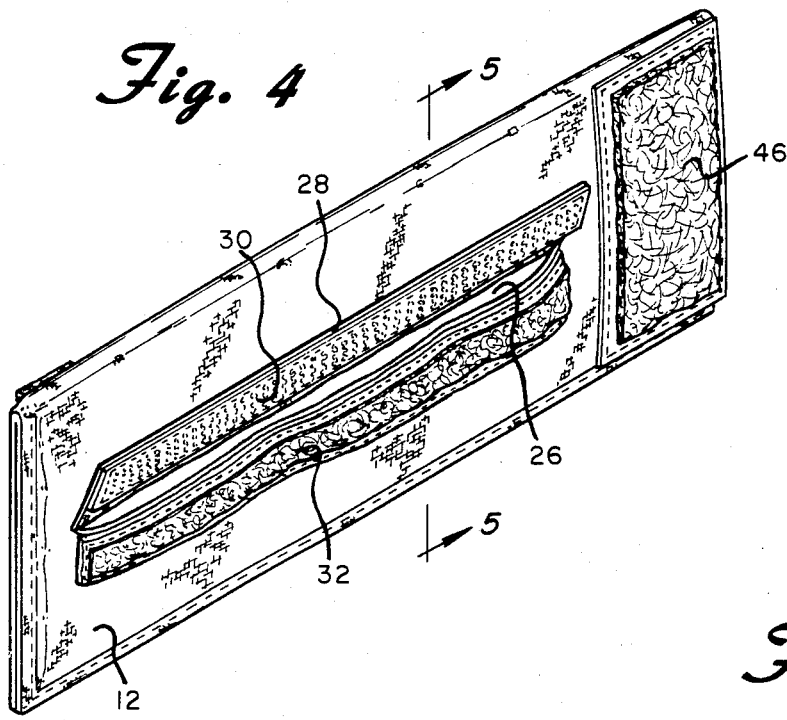
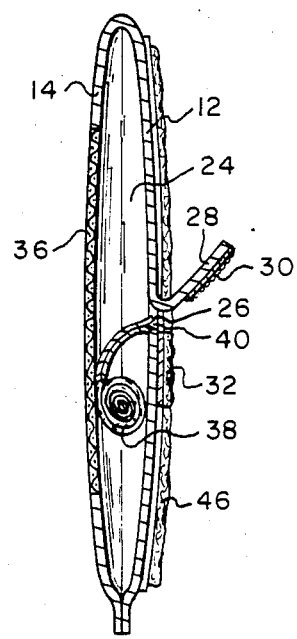
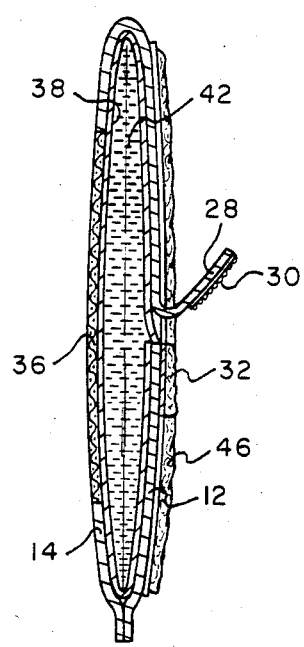

HOT OR COLD COMPRESS WITH BLADDER ENCLOSURE

BACKGROUND OF THE INVENTION

The present invention is directed toward a compress and more particularly toward a compress which can deliver either hot or cold, wet or dry temperature treatment to a person's body.

The invention is particularly useful for treating injuries such as those which may occur during participation in athletics or the like. Depending on the nature and location of the injury and the personal preferences involved, it is sometimes desirable to utilize a cold compress and sometimes desirable to utilize a hot compress. Furthermore, whether the compress is hot or cold, it is sometimes necessary that the same be kept dry. On the other hand, it is often desirable to treat the body portion with both the hot or cold temperature and moisture.

Numerous devices have been proposed in the past for applying heat or cold to a body part. Such devices are shown, for example, in U.S. Pat. Nos. 3,678,936 and 3,610,307. Similarly, prior U.S. Pat. Nos. 1,441,282 and 1,576,488 show that it has been proposed to provide devices which can apply wet compresses to a body part. Both of these patents show an ice bag which is comprised of a porous fabric material which allows water from the melting ice to pass therethrough.

While individual devices have been proposed in the past for providing either hot or cold, wet or dry temperature treatment to a body part, no one device known to Applicant has ever been proposed which is capable of selectively supplying all of these. As a result, it has been necessary, heretofore, to maintain more than one such product on hand.

SUMMARY OF THE INVENTION

The present invention overcomes the deficiencies of the prior art and provides a compress which is capable of delivering hot or cold, wet or dry temperature treatment to a person's body. The compress is formed from a pair of rectangularly shaped waterproof panels which are joined together around their peripheries to form a hollow space therebetween. One of said panels has an elongated opening to allow for the introduction of ice, hot water, a wet towel or the like and also carries a closure flap for closing the opening. The other panel has a portion thereof formed of a porous fabric material so that liquid from within the hollow space can seep therethrough. Located within the hollow space is a flexible waterproof bladder which also has an opening adjacent the opening in the panel. If a dry compress is desired, the bladder is expanded to fill the space between the panels and is filled with ice or hot water. If a wet compress is desired, the bladder is rolled or folded out of the way and ice or a hot wet towel is placed directly into the space between the panels. The compress can be wrapped around a person's leg or arm and held in place with Velcro fasteners carried by the panels.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 4 is a view similar to FIG. 2 but showing the closure flap in its open position;

FIG. 5 is a cross-sectional view taken through the line 5—5 of FIG. 4 showing the compress in one condition, and FIG. 6 is a cross-sectional view similar to FIG. 5 but showing the compress in a second condition.

DETAILED DESCRIPTION OF THE PREFERRED EMBODIMENT

Figure 1:
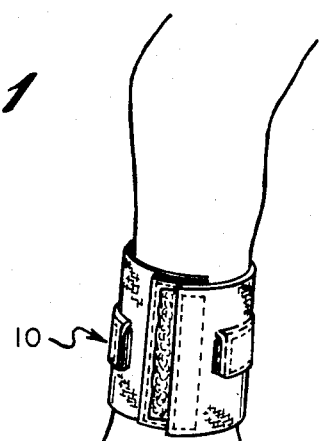
FIG. 1 is a perspective view of a hot or cold compress constructed in accordance with the principles of the present invention and shown wrapped around a person's leg.
Figure 2:
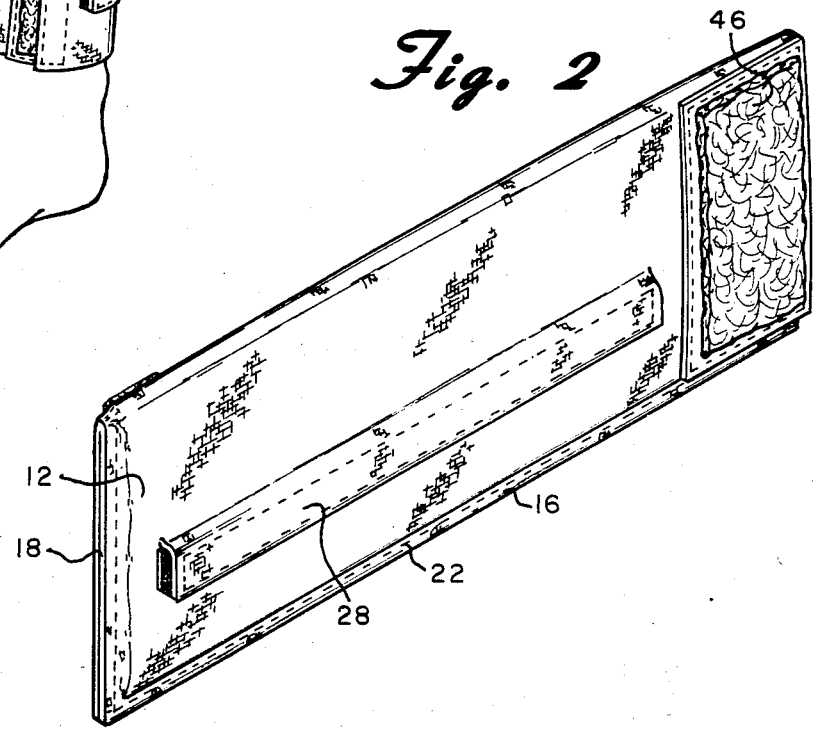
FIG. 2 is a front view of the compress shown in FIG. 1 in its extended condition.

Referring now to the drawings in detail wherein like reference numerals are used throughout the various figures to designate like elements, there is shown in each of the figures a compress constructed in accordance with the principles of the present invention and designated generally as 10. FIG. 1 shows the compress 10 being worn around a person's leg whereas the remaining figures show the compress in its fully open position.

Compress 10 is preferably made from a single sheet of material which is folded over upon itself to form a pair of substantially elongated rectangularly shaped panels 12 and 14. The front panel 12 and rear panel 14 are secured together along the bottom edge 16 and side edges 18 and 20 by way of stitching 22 or the like so as to form a hollow space 24 therebetween.

The panels 12 and 14 are preferably made from a flexible waterproof material. It is possible to make both panels entirely from a waterproof material or to make them from substantially any flexible material and to line or coat the inside with a waterproof material.

As shown most clearly in FIGS. 4 and 5, the front panel 12 has an elongated opening 26 formed therein. It is through this opening 26 that ice or other material can be inserted into the opening 24. An elongated flap 28 of flexible material is secured to the front panel 12 just above the opening 26 and includes a strip of Velcro material 30 thereon. Cooperating Velcro material 32 is mounted on the panel 12 just below the opening 26 to cooperate with the material 30 so that the flap 28 functions as a closure member to close the opening 26.

Figure 3:
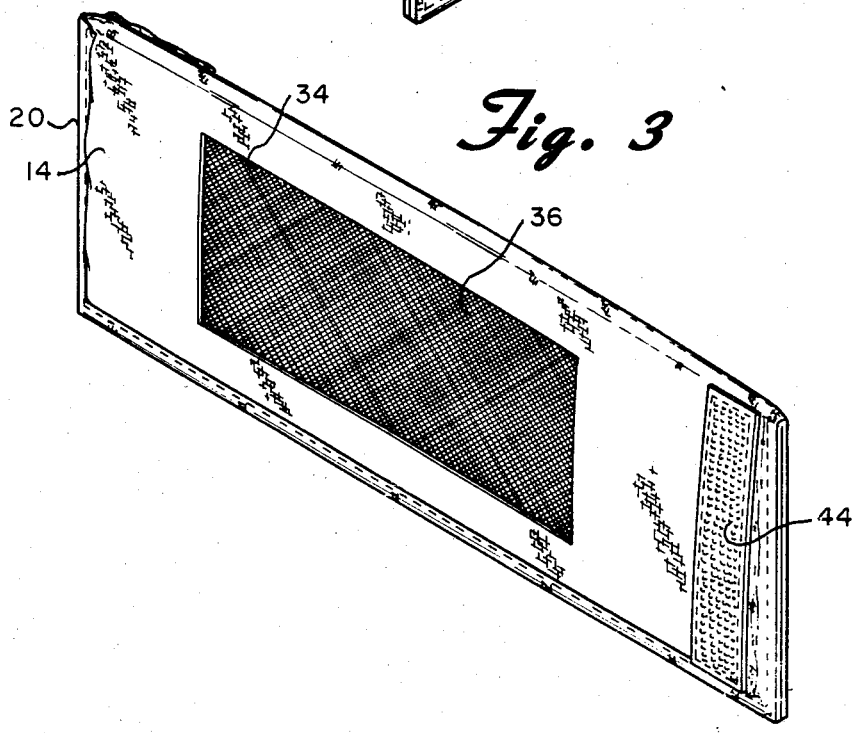
FIG. 3 is a view similar to FIG. 2 showing the reverse side thereof.

As shown most clearly in FIG. 3, a portion of the rear panel 14 is cut out from a window 34. Fitted into this window 34 and secured to the panel 14 is a flexible sheet of a porous fabric material 36. From FIG. 5, it can be seen that the inner face of fabric 36 faces space 24 while the outer face of fabric 36 is part of the exterior of compress 10. This material 36 may be made from a nylon mesh or the like which would allow liquid such as water from ice melting within the space 24 to seep out through the back of the compress 10 to the exterior thereof.

A bladder 38 is also located within the space 24 between the front and rear panels 12 and 14. Bladder 38 is made from a highly flexible totally waterproof material and has a configuration which is complementary to the shape of the inside of the panels 12 and 14. An opening 40 in the bladder 38 is accessible from the opening 26 so that the bladder can be filled through the opening 26 in the panel 12. As shown in FIGS. 5 and 6, the bladder 38 can either be rolled or folded and essentially moved out of the way so that the space 24 can be filled or the bladder 38 itself can be filled with water 42 or the like wherein the bladder will expand to fill the inside of the compress. Suitable watertight means such as a plastic zipper or interlocking seal or the like can be used to close the opening in the bladder 38.

Connected to the end of the rear surface 14 is a strip 44 of hook material. Secured to the opposite end of the front panel 12 is a patch 46 of loop or pile material. The hook and loop material utilized in the preferred embodiment is sold under the trademark Velcro which is representative of the fasteners which may be used. This patch 46 should be large enough so that the hook material 44 can catch in a number of different positions so that the size of the compress 10 can be adjusted. In lieu of the patch 46, the front surface of the panel 12 can be entirely covered with a flannel material or the like so that the Velcro hooks 44 can be secured anywhere along the front panel 12. As shown in FIG. 1, the compress 10 can be used by placing the fabric material 36 over the area to be treated and wrapping the panels around the limb securing the same thereto by attaching the Velcro hooks 44 to the patch 46.

As stated above, the compress 10 can be utilized for both hot, cold, dry and wet treatments. For dry treatments, the bladder 38 is utilized. Ice or cold water can be inserted into the bladder 38 through the opening 40 therein and the same expanded to fill the space 24. Since the bladder 38 is totally waterproof, no liquid will pass through the fabric material 36 or anywhere else through the panels 12 and 14. For wet cold, the bladder 38 is folded or rolled as shown in FIG. 5 and ice can be inserted into the space 24. This will supply cold through the rear panel 14 and as the ice melts, moisture will pass through the fabric 36. Similarly, if a hot wet compress is desired, a hot wet towel or similar item can be inserted into the space 24 through the opening 26 and both heat and moisture will then pass through the fabric material 36.

The present invention may be embodied in other specific forms without departing from the spirit or essential attributes thereof and accordingly reference should be made to the appended claims rather than to the foregoing specification as indicating the scope of the invention.

I claim:

1. A compress comprising:

a pair of elongated waterproof panels secured together around their extreme panel peripheries so as to form a hollow space therebetween;

one of said panels being substantially waterproof and having an elongated opening therein providing communication to said hollow space;

means carried by said one panel for closing said opening;

the other of said panels also being substantially waterproof but having a substantially centrally located portion thereof formed of a porous fabric material to allow liquid which may be in said space to seep out through said fabric portion to the exterior of said compress;

a totally waterproof flexible bladder means forming an enclosure secured to said one panel within said space, said bladder having a configuration complementary to said panels and having an access opening adjacent the opening in said one panel, said bladder means being so constructed and arranged so that it can either be filled and extended to fill said space or said bladder means can be collapsed and moved out of the way so that the space can be directly filled;

hook fastener means carried by one of said panels and attachable to loop fastener means carried by the other of said panels so that said compress can be wrapped around a body member and secured thereto by attaching the hook and loop means together.

* * * * *